US007304153B1

(12) United States Patent
Appleby et al.

(10) Patent No.: US 7,304,153 B1
(45) Date of Patent: Dec. 4, 2007

(54) POLYOL POLYESTER SYNTHESIS

(75) Inventors: Donald Benjamin Appleby, Ascot (GB); David Joseph Bruno, Jr., Hamilton, OH (US); Patrick Joseph Corrigan, Cincinnati, OH (US); John Keeney Howie, Oregonia, OH (US); Ju-Nan Kao, Cincinnati, OH (US); Scott David Pearson, Mason, OH (US); Richard Gerard Schafermeyer, Cincinnati, OH (US); Glen Reid Wyness, Cincinnati, OH (US)

(73) Assignee: The Procter and Gamble Co., Cincinnati, OH (US)

( * ) Notice: Subject to any disclaimer, the term of this patent is extended or adjusted under 35 U.S.C. 154(b) by 0 days.

(21) Appl. No.: 08/360,184

(22) Filed: Dec. 20, 1994

Related U.S. Application Data

(63) Continuation of application No. 08/166,658, filed on Dec. 13, 1993, now abandoned, which is a continuation of application No. 07/932,275, filed on Aug. 19, 1992, now abandoned, which is a continuation of application No. 07/580,706, filed on Sep. 11, 1990, now abandoned.

(51) Int. Cl.
C07H 13/02 (2006.01)
C07H 13/12 (2006.01)
C07H 15/04 (2006.01)
C07H 1/00 (2006.01)

(52) U.S. Cl. .................. 536/119; 536/115; 536/120; 536/124

(58) Field of Classification Search ............... 536/119, 536/115, 120, 124
See application file for complete search history.

(56) References Cited

U.S. PATENT DOCUMENTS

| 2,893,990 | A |   | 7/1959  | Hass et al. ............... 260/234 |
|-----------|---|---|---------|------------------------------------|
| 2,948,717 | A |   | 8/1960  | Babayan et al. .......... 260/234   |
| 3,251,827 | A |   | 5/1966  | Schnell et al. ........... 260/234  |
| 3,558,597 | A |   | 1/1971  | Von Brachel et al. .... 260/234    |
| 3,567,396 | A | * | 3/1971  | Setzler .................... 422/193 |
| 3,600,186 | A |   | 8/1971  | Mattson et al. ............. 99/1   |
| 3,644,333 | A | * | 2/1972  | Osipow et al.                       |
| 3,679,368 | A | * | 7/1972  | Balint et al. ............. 422/193  |
| 3,689,461 | A | * | 9/1972  | Balint et al. ............. 422/134  |
| 3,714,144 | A | * | 1/1973  | Feuge et al. .............. 536/119  |
| 3,792,041 | A |   | 2/1974  | Yamagishi et al. ........ 260/234   |
| 3,963,699 | A |   | 6/1976  | Rizzi et al. ............... 260/234 |
| 4,005,196 | A |   | 1/1977  | Jandacek et al. ........... 424/180 |
| 4,032,702 | A |   | 6/1977  | James ...................... 536/119 |
| 4,298,730 | A | * | 11/1981 | Galleymore et al. ....... 536/119   |
| 4,334,061 | A |   | 6/1982  | Bossier .................... 536/119  |
| 4,449,828 | A | * | 5/1984  | Mansour ................... 422/119  |
| 4,517,360 | A | * | 5/1985  | Volpenhein ................ 536/119  |
| 4,518,772 | A | * | 5/1985  | Volpenhein ................ 536/119  |
| 4,611,055 | A |   | 9/1986  | Yamamoto et al. ......... 536/119   |
| 4,778,881 | A |   | 10/1988 | Nieuwenhuis et al. ...... 523/119   |
| 4,968,791 | A | * | 11/1990 | Van Der Plank ............ 536/119   |
| 4,973,682 | A | * | 11/1990 | Willemse .................. 536/119  |
| 5,043,438 | A |   | 8/1991  | Buter ....................... 536/119 |
| 5,135,573 | A |   | 8/1992  | van den Berg et al. ....... 75/739  |

FOREIGN PATENT DOCUMENTS

| DE | 25 03 195  |   | 7/1976  |
|----|------------|---|---------|
| EP | 190779     |   | 6/1986  |
| EP | 0235836    |   | 9/1987  |
| EP | 254376     |   | 1/1988  |
| EP | 0256585    |   | 2/1988  |
| EP | 320043     |   | 6/1988  |
| EP | 0301634    |   | 2/1989  |
| EP | 301634     |   | 2/1989  |
| EP | 0315265    |   | 5/1989  |
| EP | 315265     |   | 5/1989  |
| EP | 0319091    |   | 6/1989  |
| EP | 319091     |   | 6/1989  |
| EP | 0319092    |   | 6/1989  |
| EP | 0320043    |   | 6/1989  |
| EP | 0322971    |   | 7/1989  |
| EP | 0323670    |   | 7/1989  |
| EP | 349059     | * | 1/1990  |
| EP | 0349059    |   | 1/1990  |
| EP | 383404     |   | 8/1990  |
| GB | 1250204    |   | 10/1971 |
| GB | 1399053    |   | 6/1975  |
| JP | 50-135016  |   | 10/1975 |
| JP | 51-14486   | * | 5/1976  |
| JP | 61-106589  |   | 5/1986  |

OTHER PUBLICATIONS

Rizzi And Taylor, "A Solvent-Free Synthesis of Sucrose Polyesters," *Journal of the American Oil Chemist's Society*, vol. 55, pp. 398-401 (1978).*

(Continued)

*Primary Examiner*—Shaojia Anna Jiang
*Assistant Examiner*—Everett White
(74) *Attorney, Agent, or Firm*—Stephen T. Murphy; Kim W. Zerby

(57) ABSTRACT

Polyol polyesters useful as nondigestible fat substitutes are prepared by improved heterogeneous interesterification processes between fatty acid esters of easily removable alcohol and polyol characterized by having one or more improvements such as using low levels of soap emulsifying agent, catalyst, and/or excess fatty acid ester; reducing the size of the polyol by mechanical means; removing extraneous particulate material during the reaction; using low temperature and/or high pressure and compensating by increasing the mass transfer area; and/or using backmixing in the initial stage(s) and plug-flow conditions in the final stage(s).

76 Claims, No Drawings

OTHER PUBLICATIONS

Fuege, Zeringue, Weiss and Brown, "Preparation of Sucrose Esters By Interesterification," *Journal of the American Oil Chemists' Society*, vol. 47, pp. 56-60 (1970).*

Felder et al. *Elementary Principles of Chemical Process*, p. 82 (Wiley 1978).*

McCabe and Smith, Unit Operations of Chemical Engineering, 3d Ed., p. 66 (McGraw-Hill, 1976).*

Sugar Esters, Osipow et al., The Journal of the American Oil Chemists' Society (JAOCS) vol. 34, pp. 185-188, Apr. 1957.

Preparation of Sucrose Esters by Interesterification, Feuge et al. JAOCS, vol. 47, pp. 56-60, Feb. 1970.

Nebraska-Snell Process, Speech by Kammerlohr.

A Solvent-free Synthesis of Sucrose Polyester, Rizzi and Taylor, JAOCS, vol. 55, pp. 398-401, Apr. 1978.

Sucrose Ester Surfactants—A Solventless Process and the Products Thereof, Parker et al., Sucrochemistry (Publication details not available at this time).

* cited by examiner

POLYOL POLYESTER SYNTHESIS

This is a continuation of application Ser. No. 08/166,658, filed on Dec. 13, 1993 now abandoned, which was a continuation of Ser. No. 07/932,275, filed Aug. 19, 1992 now abandoned, which was a continuation of Ser. No. 07/580,706 filed Sep. 11, 1990 now abandoned.

TECHNICAL FIELD

This invention relates to improved synthesis of higher polyol fatty acid polyesters, especially sucrose polyesters, and more especially via transesterification reactions that do not use a solvent to form a homogeneous reaction mix, and preferably, and more specifically to a continuous process that is capable of making said polyesters more efficiently and/or making said polyesters of improved quality.

BACKGROUND OF THE INVENTION

Processes for preparing polyol fatty acid polyesters, including processes that utilize solvent-free transesterification reactions, have been described in U.S. Pat. Nos. 3,963,699, Rizzi et al., issued Jun. 15, 1976; 4,517,360, Volpenhein, issued May 14, 1985; and 4,518,772, Volpenhein, issued May 21, 1985. Additional patents describing processes for preparing lower and higher esters of polyols include U.S. Pat. Nos. 2,893,990, Hass et al., issued Jul. 7, 1959; 3,251,827, Schnell et al., issued May 17, 1966, which discloses that the particle size of the sugar should be kept small to avoid formation of higher esters; 3,558,597, Brachel et al., issued Jan. 26, 1971; 3,644,333, Osipow et al., issued Feb. 22, 1972; 3,792,041, Yamagishi et al., issued Feb. 12, 1974, which discloses making a solution of sucrose and fatty acid, soap in water and adding the fatty acid ester and catalyst before elevating the temperature to drive off the water; 4,032,702, James, issued Jun. 28, 1977, which discloses using lower esters of sucrose as emulsifiers in the preparation of lower esters and the use of soap as a catalyst for such reactions; 4,298,730, Galleymore et al., issued Nov. 3, 1981, which also discloses the use of soap as an emulsifier and catalyst; 4,334,061, Bossier et al., issued Jun. 8, 1982, which discloses the use of a water washing step to purify the polyol polyester and incidentally discloses the use of inert gas sparging to remove lower alcohol from the reaction between sucrose and lower alkyl ester of fatty acid to speed the reaction and the removal of unreacted sucrose from an initial stage of a batch reaction for no indicated reason; and 4,877,871, Klemann et al., issued Oct. 31, 1989. All of said above patents are incorporated herein by reference.

Many of the above patents teach processes that use a solvent to assist in the formation of a homogeneous reaction mixture. However, the presence of the solvent is not desirable since it must then be removed. Also, many of the above processes primarily relate to the preparation of lower esters, containing one or two ester groups, that are desirable for use as surfactants. The present processes primarily relate to the preparation of polyol polyesters that have high degrees of esterification, preferably polyesters that are more than about 50% esterified, i.e., at least about 50% of the total number of available hydroxy groups on the polyol are esterified with a fatty acyl radical.

In order to have a better commercial process for preparing highly esterified polyols, it is desirable to have a process that is fast, preferably continuous, and that results in a minimum of unwanted materials that have to be removed.

SUMMARY OF THE INVENTION

The present invention relates to improved, preferably continuous, processes for preparing highly esterified polyol fatty acid polyester by interesterifying (a) polyol containing more than about four esterifiable hydroxy groups and (b) fatty acid ester of easily removable alcohol, in a heterogeneous reaction mixture, e.g., in the absence of any substantial amount of unreactive solvent, wherein each of said processes comprises at least one improvement selected from the group consisting of:

(1) The polyol used to prepare the said polyester is preferably particulate solid, preferably sucrose, that has had its particle size reduced by mechanical size reduction, e.g., grinding, to a particle size of less than about 100 microns, preferably less than about 50 microns, and more preferably less than about 10 microns;

(2) The process is a continuous process in which the initial catalyst level is from about 0.01 to about 0.5 mole of catalyst per mole of polyol, preferably from about 0.01 to about 0.1 mole of catalyst per mole of polyol;

(3) The initial level of soap emulsifier in the first stage of the reaction is from about 0.001 to about 0.6, preferably from about 0.2 to about 0.4 moles per mole of polyol;

(4) After the degree of esterification is greater than about 60% and at least some of any soap emulsifier that is present is insoluble in the reaction mixture, removing the insoluble soap, and any other large particles, e.g., by filtration, preferably in a continuous process;

(5) Any unreacted polyol, e.g., sucrose, and any catalyst having particle sizes above about 1 micron are removed, e.g., by filtration, before the degree of esterification reaches about 75%, and preferably after it has reached 15%, more preferably after 40%, and before any substantial amount of soap emulsifier present has become insoluble in the reaction mixture, preferably in a continuous process;

(6) The molar ratio of the total ester reactant to each esterifiable hydroxy group in the polyol in the reaction is from about 0.9:1 to about 1.4:1, preferably from about 1:1 to about 1.2:1;

(7) The temperature in the initial stage of the reaction is maintained at from about 265° F. to about 285° F., preferably from about 270° F. to about 275° F. (from about 132° C. to about 140° C., preferably from about 132° C. to about 135° C.), and the temperature in the final stages of the reaction is from about 175° F. to about 275° F., preferably from about 210° F. to about 250° F. (from about 80° C. to about 135° C., preferably from about 100° C. to about 120° C.), though the temperature in the final stages can be as high as about 325° F. (about 165° C.) if unreacted polyol is not present;

(8) The said easily removable alcohol is a volatile alcohol, the reactor pressure is maintained at from about 5 to about 300 mm Hg, preferably from about 15 to about 100 mm Hg, and the removal of the volatile alcohol produced by the reaction between the ester reactant and the polyol is assisted by increasing the mass transfer area of the reaction mixture by increasing the surface area in the reactor and/or sparging, e.g., with an inert gas such as nitrogen, low molecular weight hydrocarbons, carbon dioxide, etc., to reduce the volatile alcohol's partial pressure;

(9) The initial stage of the reaction, and especially in a continuous process that uses multiple reaction vessels, is carried out under conditions, e.g., of backmixing, to maintain a level of lower partial esters of said polyol in an emulsifying amount, typically corresponding to an average degree of esterification of the polyol of from about 10% to about 70%, preferably more than about 20%, more preferably from about 30% to about 60%. Backmixing is preferred, either within the reaction vessel, as a result of the hydrodynamics that are characteristic of a backmix reactor, or by recycling a portion of the reaction mixture, or, more preferably, by using two backmix reactors in series for the initial stage, with the product of the first reactor in the initial stage having a degree of esterification of from about 30% to about 50%, and the product of the second reactor having a degree of esterification of from about 50% to about 60%;

(10) The final stage, or stages, of the reaction are carried out under conditions that at least approach plug-flow, including batch conditions, after the degree of esterification of said polyol has reached at least about 50% to achieve a final degree of esterification of at least about 70%, preferably at least about 95%; and

(11) Mixtures thereof.

DETAILED DESCRIPTION OF THE INVENTION

The Polyol

As used herein, the term "polyol" is intended to include any linear, cyclic, or aromatic compound containing at least four free esterifiable hydroxyl groups. In practicing the process disclosed herein, sucrose is the most highly preferred polyol. If sucrose is not used, then the selection of a suitable alternative polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, insulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups be changed to alcohol groups or reacted with alcohol groups to form ether linkages.

Particularly preferred classes of materials suitable for use herein include the monosaccharides, the disaccharides and sugar alcohols: Preferred carbohydrates and sugar alcohols include xylitol, sorbitol, and sucrose. The most preferred is sucrose.

Fatty Acid Ester of Easily Removable Alcohol

As used herein, the terms "fatty acid ester(s)" and "ester reactant(s)" are intended to include any compound wherein the alcohol portion is easily removed, including polyols and substituted alcohols, etc., but are preferably esters of volatile alcohols, e.g., the $C_1$-$C_4$ (preferably methyl), 2-methoxy ethyl and benzyl esters of fatty acids containing about eight or more carbon atoms, and mixtures of such esters. Volatile alcohols are highly desirable. Methyl esters are the most highly preferred ester reactants. Suitable ester reactants can be prepared by the reaction of diazoalkanes and fatty acids, or derived by alcoholysis from the fatty acids naturally occurring in fats and oils.

Suitable fatty acid esters can be derived from either synthetic or natural, saturated or unsaturated fatty acids and include positional and geometrical isomers. Suitable preferred saturated fatty acids include, for example, caprylic, capric, lauric, myristic, palmitic, stearic, arachidic, behenic, isomyristic, isomargaric, myristic, caprylic, and anteisoarachadic. Suitable preferred unsaturated fatty acids include, for example, myristoleic, palmitoleic, ricinoleic, linoleic, oleic, elaidic, linolenic, eleasteric, arachidonic, erucic, and erythrogenic acids. Mixtures of fatty acids derived from soybean oil, palm oil, safflower oil, rapeseed oil, canola (low erucic acid), and corn oil are especially preferred for use herein. The fatty acids can be used "as is," and/or after hydrogenation, and/or isomerization, and/or purification. For example, rapeseed provides a good source for $C_{22}$ fatty acid. $C_{16}$-$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

Some useful solid polyol fatty acid polyesters are those wherein the ester groups comprise a combination of: (i) long chain, unsaturated fatty acid radicals and/or short chain saturated fatty acid radicals, and (ii) long chain saturated fatty acid radicals, the ratio of (i):(ii) being from about 1:15 to about 2:1, and wherein at least about 15% (preferably at least about 30%, more preferably at least about 50%, and most preferably at least about 60%) by weight of the total fatty acid radicals in the solid polyol polyester are $C_{20}$ or higher saturated fatty acid radicals. The long chain unsaturated fatty acid radicals are typically, but not necessarily, straight chain (i.e., normal) and contain at least about 12 (preferably about 12 to about 26, more preferably about 18 to 22) carbon atoms. The most preferred unsaturated radicals are the $C_{18}$ mono and/or diunsaturated fatty acid radicals. The short chain saturated fatty acid radicals are typically, but not necessarily, normal and contain 2 to 12 (preferably 6 to 12 and most preferably 8 to 12) carbon atoms. The long chain saturated fatty acid radicals are typically, but not necessarily, normal and contain at least 20 (preferably 20 to 26, most preferably 22) carbon atoms. The molar ratio of Group (i) fatty acid radicals to Group (ii) fatty acid radicals in the polyester molecule is from about 1:15 to about 2:1 (preferably from about 1:7 to about 5:3; more preferably from about 1:7 to about 3:5). A typical suitable range is about 3:5 to 4:4. The average degree of esterification of these solid polyol fatty acid polyesters is such that at least 4 of the hydroxyl groups of the polyol are esterified. In the case of sucrose polyesters, from about 7 to 8 of the hydroxyl groups of the polyol are preferably esterified. Typically, substantially all (e.g., at least 85%, preferably at least 95%) of the hydroxyl groups of the polyol are esterified.

Some especially useful solid polyol polyesters prepared by the processes herein contain a combination of: (i) long chain (at least 12 carbon atoms) unsaturated fatty acid radicals, or a mixture of said radicals and saturated short chain ($C_2$-$C_{12}$) fatty acid radicals, and (ii) long chain (at least 20 carbon atoms) saturated fatty acid radicals, in a molar ratio of (i) to (ii) of from about 1:15 to about 2:1, and wherein at least four of the hydroxyl groups of the polyol are esterified.

These solid polyol fatty acid polyesters can be used as "thickening agents" or "hardstocks" for blending with liquid digestible or nondigestible oils in the formulation of cooking and salad oils or semi-solid fat products such as shortenings, as well as other food products which contain a combination of fat and non-fat ingredients, e.g., margarines, mayonnaise, frozen dairy desserts and the like. Further, this high capacity to thicken liquid oils makes such compounds, having a melting point above body temperature (37° C.), particularly useful in the formulation of food products containing the nondigestible oils so as to control or prevent the passive oil loss problem associated with the ingestion of such oils.

Examples of long chain unsaturated and polyunsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and diunsaturated fatty acid radicals are preferred.

Examples of suitable short chain saturated fatty acid radicals are acetate, butyrate, (caproate), hexanoate (caprylate), decanoate (caprate) and dodecanoate (laurate). Use of more volatile ester reactants may require modification of the process, e.g., use of reflux in the reactors or other means to prevent excessive loss of said reactants.

Examples of suitable long chain saturated fatty acid radicals are eicosanoate (arachidate), docosanoate (behenate), tetracosanoate (lignocerate), and hexacosanoate (cerotate).

Of course, the long chain unsaturated fatty acid radicals can be used singly or in mixtures with each other or in mixtures with the short chain saturated fatty acid radicals, in all proportions. Likewise, the long chain saturated acid radicals can be used in combination with each other in all proportions. Mixed fatty acid radicals from source oils which contain substantial amounts of the desired unsaturated or saturated acids can be used as the fatty acid radicals to prepare compounds of the invention. The mixed fatty acids from the oils should contain at least about 30% (preferably at least about 50%, and most preferably at least about 80%) of the desired unsaturated or saturated acids. For example, rapeseed oil fatty acids or soybean oil fatty acids can be used instead of pure $C_{12}$-$C_{26}$ unsaturated fatty acids. Hardened (i.e., hydrogenated) high erucic rapeseed oil fatty acids can be used instead of pure $C_{20}$-26 saturated acids. Preferably the $C_{20}$ and higher acids (or their derivatives, e.g., methyl esters) are concentrated, for example by distillation. The fatty acids from palm kernel oil or coconut oil can be used as a source of $C_8$ to $C_{12}$ acids. An example of the use of source oils to make solid polyol polyesters of the invention is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated $C_{18}$ acid radicals to $C_{20}$ and higher saturated acid radicals of about 1:1 and 28.6 weight percent of the total fatty acids in the polyester will be $C_{20}$ and $C_{22}$ fatty acids.

The higher the proportions of the desired unsaturated and saturated acids in the fatty acid stocks used in making the solid polyol polyester, the more efficient the ester will be in its ability to bind liquid oils, including nondigestible oils.

As stated above, some preferred unsaturated fatty acid radicals are those which have 18 carbon atoms, and are mono- and/or diunsaturated. Preferred short chain fatty acid radicals are those which have 8-12 carbon atoms. The preferred long chain saturated fatty acid radical is behenate. Preferred solid polyol polyesters of the invention are polyesters of sucrose in which at least 7 of the 8 hydroxyl groups are esterified.

Examples of such solid polyol polyesters are sorbitol hexaester in which the acid ester radicals are palmitoleate and arachidate in a 1:2 molar ratio; the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7-8, and in which the fatty acid radicals are $C_{18}$ mono- and/or diunsaturated and behenic, in a molar ratio of unsaturates:behenic of from about 1:7 to about 3:5.

The said solid polyol polyesters preferably have complete melting points above about 25° C., more preferably above about 37° C., even more preferably above about 50° C. and most preferably above about 60° C. Melting points reported herein are measured by Differential Scanning Calorimetry (DSC). These solid materials have the ability to trap relatively large amounts of oil within their crystal structure. As a consequence, they can be used as "hardstocks" by blending them in amounts of from about 1% to about 50% (typically from about 1% to about 25%) with liquid oils, including those described in the patents incorporated hereinbefore by reference, to prepare semi-solid compositions such as shortenings and margarines. A typical suitable range is from about 10% to about 25%. The oils for these compositions can be conventional digestible triglyceride oils such as cottonseed, corn, canola, or soybean oil, or nondigestible edible oils. The solid polyol polyesters of the invention having complete melting points above about 37° C. can be blended at levels of as low as about 1% (preferably at least about 2%) with liquid nondigestible oils having complete melting points below about 37° C. in order to control passive oil loss upon ingestion of food compositions containing the nondigestible oil.

As disclosed hereinbefore, other suitable polyol polyesters that can be prepared by the processes herein include the polyol polyesters disclosed in the patents incorporated herein by reference, especially U.S. Pat. Nos. 3,963,699; 4,517,360; and 4,518,772.

The fatty acid composition (FAC) of the polyol polyesters can be determined by gas chromatography, using a Hewlett-Packard Model 5712A gas chromatograph equipped with a thermal conductivity detector and a Hewlett-Packard Mode 17671A automatic sampler. The chromatographic method used is described in *Official Methods and Recommended Practices of the American Oil Chemists Society*, 3rd Ed., 1984, Procedures 1-$C_e$62 (incorporated herein by reference).

It is very important for the preparation of improved polyol polyesters that the fatty acid esters be highly purified to remove color/odor materials, oxidation products, and/or their precursors. Such materials include those that have a color, odor, or taste that is objectionable, or which develop an objectionable color, odor, or taste upon heat treatment and/or oxidation. In addition, highly polar materials which coat the catalyst surface should be removed. Preferably, the carbonyl value should be less than about 200 ppm, more preferably less than about 100 ppm, and even more preferably less than about 50 ppm. Processes for preparing such fatty acid esters are disclosed in U.S. Pat. No. 4,931,552, Gibson et al., issued Jun. 5, 1990, said patent being incorporated herein by reference. The percent transmittance at 375 nm with a heptane standard should be greater than zero, preferably greater than about 60, most preferably greater than about 80. For typical ester sources without added colored materials, these values define operable reactants. I.e., the carbonyl content is generally indicative of the total level of polar materials present. The low level of color/odor materials and/or oxidation products in the reactants helps provide improved color polyol polyester products that can be further improved by a combination of the process improvements set forth herein.

Alkali Metal Fatty Acid Soap

Alkali metal soaps are typically, and preferably, used as emulsifiers in the processes described herein. For solid polyols, like sucrose, such soaps are believed to be essential. As used herein, the term "alkali metal fatty acid soap" is intended to include the alkali metal salts of saturated and unsaturated fatty acids having from about 8 to about 18 carbon atoms. Accordingly, suitable alkali metal fatty acid soaps include, for example, the lithium, sodium, potassium, rubidium, and cesium salts of the fatty acids described hereinbefore. Mixtures of fatty acids derived from soybean oil, sunflower oil, safflower oil, and corn oil are preferred for use herein. Accordingly, preferred alkali metal fatty acid soaps include, for example, the potassium soap made from soybean oil fatty-acids.

In a preferred process of reacting sucrose and, especially, the methyl esters of soybean oil fatty acids, it is highly desirable that any soap present be an alkali metal, e.g., potassium or sodium, preferably potassium, salt of hydrogenated fatty acids containing from about 16 to about 22 carbon atoms.

Catalyst

The basic catalysts generally suitable for use in preparing the polyol polyesters described herein are those selected from the group consisting of alkali metals, such as sodium, lithium and potassium: alloys of two or more alkali metals, such as sodium-lithium and sodium-potassium alloys; alkali metal hydrides, such as sodium, lithium and potassium hydride; and alkali metal alkoxides, such as potassium t-butoxide, potassium methoxide, and/or sodium methoxide. Potassium methoxide is preferred, especially when used with potassium soap.

In another particularly preferred embodiment of the present invention, the basic catalyst used in the reaction is potassium carbonate, sodium carbonate, barium carbonate, or mixtures of these compounds having particle sizes that are less than about 100 microns, preferably less than about 50 microns, as discussed more fully hereinafter. It has been found that when these specific compounds are used as catalysts, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed and claimed in U.S. Pat. No. 4,517,360, Volpenhein, issued May 14, 1985, entitled "Synthesis of Higher Polyol Fatty Acid Polyesters using Carbonate Catalysts," said patent being incorporated herein by reference.

More reactive catalysts such as potassium or sodium methoxide should be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$-$C_{22}$ fatty acids. Addition of these more alkaline, reactive catalysts in the later stages after the polyol has an average degree of esterification of more than about 60%, preferably more than about 85%, provides improved reaction kinetics and results in a greater degree of esterification of the polyol yet does not create the level of color/odor materials that would be created if such catalysts were present from the start of the reaction.

The level of catalyst is kept as low as possible, as discussed more fully hereinafter, typically from about 0.01 to about 0.5, preferably from about 0.01 to about 0.1, more preferably from about 0.02 to about 0.05, moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first phase of the reaction, and/or the destruction and removal of the catalyst after the reaction has reached the desired end point.

The Improvements (1) The Small Particle Size Polyol Obtained by Mechanical Size Reduction The use of small particle size polyol, e.g., sucrose, in esterification reactions to form polyol polyesters is highly desirable to improve the speed of reaction. In reactions that use a solvent to form a homogeneous reaction mixture, there is little need for the small particle size, since the polyol is dissolved by the solvent. However, in solventless, heterogeneous reactions of the type herein, the small particle size is highly desirable. The small particle size can also be achieved by art-disclosed methods in which the polyol, e.g., sucrose, is dissolved in water and then the water is removed after the other reactant ingredients and/or catalyst are present to form small particles of the polyol in situ. There is no general consensus, or appreciation, in such art that the primary factor that improves the reaction is the resulting small particle size of the polyol. Furthermore, although this preliminary step of dissolving the polyol in water provides the desired small particle size, it requires the removal of water from the reaction mixture, usually at a time when other ingredients are present, and the presence of water can promote the formation of undesirable side products. It is especially undesirable in a continuous process.

Thus, the present development has many advantages over such processes. It is highly desirable to avoid exposing the reactants to the conditions required to remove the solvent and also to avoid the need for the apparatus/equipment needed for the removal. Also, to avoid losses, the solvent may need to be recovered or, if the solvent is water, the heat may need to be recovered. Additionally, the ingredients have to be handled while the solvent is present and that raises the capacity requirements for the process.

It has now been found that an improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, e.g., by a combination of grinding, milling, and/or sieving. It is surprising that the particles of these sizes, prepared by simple mechanical size reduction methods, provide the benefits of the prior art processes requiring formation of water solutions of, e.g., sucrose, that give particle diameters below one micron.

(2) Low Catalyst Level and Preferred Small Particle Size Catalyst in a Continuous Process It has been found that, in a continuous process, a low level of catalyst is highly desirable. Surprisingly, a low level of catalyst, e.g., below about one half of a mole per mole of polyol, still provides fast reactions with little formation of undesirable materials. The surprising speed of the reaction with a low level of catalyst permits the low level of catalyst to be used in a continuous process where a long reaction time would be costly, as disclosed hereinafter. The preferred level of catalyst is from about 0.01 to about 0.1, preferably from about 0.02 to about 0.05, mole per mole of polyol. With these levels of catalyst, the reaction proceeds at a fast rate and the amount of catalyst and/or soap, that must be removed at the end of the reaction is much less. A preferred catalyst is the small amount of base that typically accompanies soap that is also used to promote the reaction. Acceptable other catalysts have been described hereinbefore. As discussed hereinbefore, the preferred cation is potassium. Also, as discussed hereinbefore, it is often desirable to add a more active catalyst like an alkali metal alcoholate, especially $C_{1-4}$ alkoxides, more especially methoxides, and desirably sodium and/or potassium alcoholates such as potassium and/or sodium methoxide, to the reaction mixture at a later stage of the reaction to further increase the speed of the reaction.

Homogeneous catalysts are desirable for the reaction. However, solid catalysts can be used.

The preferred particle size of any solid catalyst is less than about 100 microns, preferably less than about 50 microns, and even more preferably less than about 10 microns. When low levels of catalyst are used, it is important to use smaller particle sizes of catalysts and/or sucrose.

(3) The Soap Emulsifier

Soap is a necessary ingredient for optimum reactions, especially with solid polyols, e.g., sucrose. However, it has now been found that levels of soap that are much less than those previously believed optimal are in fact desirable. Although some level of soap is necessary for optimal performance, even when there is another emulsifier present, the absolute level of soap is desirably kept low. The level of soap should be at least enough to dissolve the polyol at an acceptable rate. Therefore, the level of soap can be reduced as a result of using smaller particle polyol, e.g., sucrose, and/or reaction conditions that favor the solubilization of the polyol. Excessive soap can cause foaming. The level of soap in the first stage of the reaction is desirably from about 0.001 to about 0.6, preferably from about 0.2 to about 0.4 moles of soap per mole of polyol. This level of soap assists the polyol, especially sucrose, to dissolve in the reaction mixture. The soap is preferably used in combination with another emulsifier, preferably with the lower esters of the polyol and the fatty acid which are present either by being added as part of the initial reaction mixture, or by backmixing. Also, the soap is preferably potassium soap of hydrogenated fatty acids containing from about 10 to about 22 carbon atoms, as discussed hereinbefore.

(4) Optional Removal of Soap Emulsifier

After the average degree of esterification reaches about 60%, the soap is no longer needed to facilitate the reaction and, therefore, can be removed. The soap emulsifier is not essential after the polyol has reacted once and there is sufficient lower ester to maintain the homogeneity of the reaction mixture.

Removal of soap can be accomplished, e.g., by filtration, centrifugation, etc., since the soap is relatively insoluble in the reaction mixture at such higher degrees of esterification. The resulting filtered reaction mixture does not need to be recatalyzed, and, the reaction proceeds at a much higher rate than if the soap is present. The filtered reaction mixture typically has a soap level of less than about 0.5, preferably less than about 0.1 moles of soap per mole of polyol, more preferably less than about 0.05 moles of soap per mole of polyol. The filtered material can be returned to the initial stage of the reaction. However, since the composition of the filtered material can vary, it is usually better not to recycle it.

Removal of the soap is not desirable at very early stages of the reaction, especially when the preferred low levels of soap described herein are used. In later stages, e.g., especially after interesterification is about 60% complete, any soap that is not soluble in the reaction mix can be removed advantageously.

(5) Optional Removal of Unreacted Polyol and/or Large Particle Catalyst at an Early Stage of the Reaction Unreacted polyol and/or large particle catalyst are desirably removed at an early stage of the reaction, e.g., before the polyol is esterified to more than about 75% and, preferably, (a) after the degree of interesterification is greater than about 15%, preferably greater than about 40%, and (b) while the soap that is present is still soluble in the reaction mixture. This removal results in fast reaction kinetics and high conversion to highly esterified product having good color without the need to add additional catalyst thereafter. Accordingly, this improvement is especially desirable in continuous processes. Removal at an early stage is more convenient than in a later stage due to the low viscosity of the reaction mixture and minimizes production of unwanted by-products. Unreacted polyol, such as sucrose, can interfere with the orderly progress of the reaction in the later stages where it limits the desired interesterification reaction by degrading, and/or preferentially reacting with, the active form of the catalyst and/or by continuing to create undesirable by-products such as color bodies.

Removal of unreacted polyol and/or large size catalyst can be accomplished by, e.g., filtration and/or by centrifugation if the polyol is a solid in the reaction mixture. The resulting reaction mixture that is free of unreacted polyol will then react faster and reach the desired degree of esterification quicker than if the polyol remains. The reaction mixture prepared by, e.g., filtration, typically has an unreacted polyol content of less than about 1%, preferably less than above 0.2%, and more preferably less than about 0.05%. The filtered polyol and/or catalyst can be returned to an earlier stage of the reaction or discarded.

Unreacted polyol is preferably removed in an early stage of the reaction, while any soap emulsifier is still soluble in the reaction mixture. When the polyol is removed at an early stage, the molar ratio of soap emulsifier to polyol either remains essentially unchanged, or is slightly increased.

(6) The Low Ester/Polyol Ratio

In the reaction, it is preferable to use a molar ratio of total ester reactant to esterifiable sites on the polyol of from about 0.9:1 to about 1.4:1, preferably from about 1:1 to about 1.2:1. An advantage of this lower level of ester is that the amount of material in the reaction mixture is less, thus simplifying any manipulations and permitting the use of equipment with lower capacity for the same output while the risk of undesirable side reactions is minimized. Additionally, the control of the degree of esterification is better when the reactants are closer to the desired level, and the amount of unreacted ester that must be removed is drastically reduced.

When the total ratio of ester to esterifiable polyol sites is lower, e.g., from about 0.9:1 to about 1.4:1, and especially when said ratio is below about 1.2:1, it has now been found that high reaction completion and fast reaction can both be achieved by increasing removal of the lower alcohol. This can be accomplished by significantly increasing the mass transfer rate as compared to a simple stirred vessel of the same dimensions, by, e.g., increasing the surface area of the reactor (e.g., by adding packing), spraying the reactants, using a film reactor, and/or sparging with an inert gas. It can also be accomplished by using reduced pressure.

Using lower ratios of ester to polyol provides considerable improvement in purification of the desired polyol polyester without adversely affecting the ease with which the reaction is carried out. When these lower ratios of ester to polyol are combined with lower levels of soap and/or catalyst, and/or with removal of unreacted materials before completion of the reaction, the resulting products can be more readily cleaned up, even, e.g., without a separate water-washing step.

(7) Low Temperatures

It is highly preferable to run the reaction in the initial stages at temperatures between about 265° F. (130° C.) and about 285° F. (140° C.), preferably between about 270° F. (132° C.) and about 275° F. (135° C.) to achieve rapid initial esterification of the polyol without excessive degradation of the polyol. However, lower temperatures, e.g., from about 175° F. to about 275° F., preferably from about 210° F. to about 250° F. (from about 80° C. to about 135° C., preferably from about 100° C. to about 120° C.), are desirable in the later stages to minimize side reactions. The speed of the reaction, surprisingly, can be maintained by the use of reactors in the final stages that provide improved removal of the resulting alkanol, e.g., reactors with larger surface areas and/or sparging with an inert gas, and/or reduced pressures (e.g., below about 300 mm of Hg, as discussed hereinbefore and hereinafter.

(8) Higher Pressures

It is highly desirable to use higher reaction pressures than have been considered optimum heretofore, e.g., from about 5 mm Hg to about 300 mm Hg, preferably from about 15 to about 150 mm Hg., to avoid having to provide high capacity equipment to maintain the low pressure and to avoid the high energy requirements of maintaining low pressures. In order to maintain an acceptable speed of reaction with higher pressures, it is necessary to use reactors with high surface areas and/or improved agitation and/or sparging with an inert gas as discussed hereinbefore, to aid in the removal of the volatile alcohol that is produced in the interesterification reaction. The sparging rate and other conditions should be sufficient to maintain the partial pressure of the volatile alcohol at the desired level. In the specific case of methyl alcohol and the preparation of sucrose octaester, the partial pressure of the alcohol in the initial stage should be less than about 100 mm Hg, preferably less than about 50 mm Hg and in subsequent stages where higher degrees of esterification are achieved, the partial pressure of the methyl alcohol should be maintained at less than about 30 mm Hg, more preferably less than about 15 mm Hg, most preferably less than about 10 mm Hg.

(9) Maintaining Low Degree of Esterification in Initial Stages by Backmixing

It is highly desirable to conduct the initial stage, or stages, of the reaction under back-mixing conditions to maintain the degree of esterification between about 10% (preferably 20%) and about 70%, preferably between about 35% and about 60%. This degree of esterification provides sufficient lower partial polyol polyester to aid in the solubilization of the poorly soluble polyol and to provide a stable heterogeneous reaction mixture that minimizes unreacted polyol, and the distribution/composition and/or level of lower esters and/or soap that cause foaming is low enough to permit continuous reaction without overfoaming. Levels of conversion below about 20% can require low levels of soap and/or high pressure to avoid overfoaming. In a continuous reaction, the individual reactants can be added to the first stage at a rate that maintains the desired degree of esterification and yet provides sufficient yield from the first stage to maintain the reaction in the subsequent stage, or stages.

It is desirable in the initial stage, or stages, of the process, and especially of a continuous process, to have a relatively high degree of completion. The preferred degree of esterification is at least about 60%, more preferably at least about 75%, to minimize the amount of esterification that must take place in the final stages. As set out hereinafter, the final stages are preferably carried out under conditions of plug flow. It is highly preferable to leave as little as possible for the final stages. In the final stages, the reaction conditions are more stringent (lower pressure, higher sparge rates, etc.) and therefore more costly. Decreasing the time of the later stages and/or the size of the reactor is therefore desirable. Maintenance of the appropriate composition for solubilizing the polyol is assisted by withholding a portion of the ester reactant from this initial stage, as described in U.S. Pat. No. 3,963,699, supra, incorporated herein by reference. In the initial stage, it is preferable to use only about 30% to about 70% of the total ester reactant, with the remainder being added in the later stages, especially where there are plug flow conditions.

Backmixing can be achieved in a continuous reaction, for example, by continually recycling a portion of the first stage reaction stream and/or by carrying out the reaction in a well agitated vessel (or, e.g., two vessels in series, or any other similar configuration that has hydrodynamically similar mixing conditions) where the reactants are continually added and the product is removed at rates that maintain the desired level of esterification. Although it is possible to start with plug flow conditions, the initial solubility of sucrose is low at the start of the reaction; the risk of unacceptable levels of foam when the degree of esterification is less than about 20% is great; and the resulting instability of the reaction mixture gives variable, poorly controlled esterification of the polyol. Without filtration of the unreacted reactants as discussed hereinbefore, the conversion of the polyol can be poor and therefore plug flow is undesirable in the initial stages, especially without recycling.

The product of the first stage is preferably filtered, as discussed hereinbefore, and the unreacted solids are returned to the first stage, or, preferably, if at a lower level, discarded, since the ingredients are present, at least initially, at varying and unknown levels. If the reaction contains only low levels of soap emulsifier and catalyst, as preferred herein, the amount of material to be separated is minimal. Once steady state is achieved in a continuous reaction, the separated material can be cleaned up, e.g., by a purge stream, and recycled.

Backmixing in a batch process, can be approximated by using part of a previous batch that has the right degree of esterification, and adding reactants to the batch while the reaction is continuing until the appropriate degree of completion is reached, whereupon the addition of reactants is stopped and the reaction is taken to completion. A "semi-batch" reaction can be run by continually bringing batches to the appropriate intermediate degree of completion and then transferring at least the major portion of the batch to another vessel where the reaction is taken to completion.

Apparatus that is suitable for backmixing, and/or plug flow conditions, as discussed hereinafter, is disclosed in U.S. Pat. Nos. 3,567,396, Setzler, issued Mar. 2, 1971; 3,679,368, Balint, et al., issued Jul. 25, 1972; 4,449,828, Mansour, issued May 22, 1984; 4,472,061, Mansour, issued Sep. 18, 1984; 4,543,194, Spence et al., issued Sep. 24, 1985; and 4,615,870, Armstrong et al., issued Oct. 7, 1986, all of said patents being incorporated herein by reference. Other disclosures of suitable processes and apparatus can be found in: The Degree of Mixing in Continuous Flow Systems, Zwietering, Chemical Engineering Science, pp. 1-15, Vol. II, No. 1 (1959); Continuous Flow Stirred-Tank Reactor Systems, MacDonald and Piret, Chemical Engineering Progress, Vol. 47, No. 7, pp. 363-8 (July 1951); and Reaction Kinetics in a Tubular Reactor, Baron, Manning and Johnstone, Chemical Engineering Progress, Vol. 48, No. 3, pp. 125-132 (March 1952), all of said articles being incorporated herein by reference.

It is advantageous, for many of the improvements herein, to carry out the reaction in a series of at least two, preferably from two to about eight, more preferably from three to about eight, reaction vessels. The use of a series of reaction vessels and/or separate reactors, permits closer control over the variables that control the course of the reaction. Separate vessels/reactors allow for closer control of pressure, temperature, sparging rates, levels of reactants, etc. Separate vessels are also particularly desirable for sequential esterification with the different fatty acid chain lengths.

(10) Use of Plug-Flow and/or Batch Conditions in the Final Stages to Achieve High Degree of Complete Esterification The final stage, or stages, of the reaction should be carried out under plug-flow, or batch, conditions to prevent backmixing and thereby achieve high degrees of esterification. This plug flow can be approximated by feeding the output of the initial stage into a series of at least two continuous stirred tank reactors, but preferably is accomplished more efficiently in a continuous reactor, for example, in a tubular reactor and/or packed column and/or tray reactor and/or falling or rising film reactor, using more nearly plug-flow reactor apparatus. As discussed hereinbefore, the plug flow conditions should be used after the degree of esterification of said polyol has reached at least about 50%. The final degree of esterification should be at least about 70%, preferably at least about 98%.

The total ester reactant to polyol esterifiable site in the final stages should be from about 0.9:1 to about 1.4:1, preferably from about 1:1 to about 1.2:1. The reduction, or removal, of soap, as discussed hereinbefore, is preferred for column or film reactors to reduce the viscosity for improved operation.

(11) Combinations of Improvements

Some combinations of improvements have been discussed in the discussions of the individual improvements. In addition, there are preferred combinations as follows:

(I) In either a batch, semi-batch, or continuous process, the combination of (1) small particle size polyol, preferably obtained by mechanical size reduction to avoid the complications associated with solvent removal, (2) low levels of catalyst, preferably having a small particle size, and (3) low levels of soap, is highly desirable since such a combination provides a fast reaction while minimizing the amount of unwanted materials that are present and that must eventually be removed.

(II) Additional improvements that are preferably combined with the three improvements of (I) above are: (6) the use of a very low ratio of ester reactant to polyol and (9) the use of lower partial esters of the polyol, preferably maintained by backmixing, to aid in dissolving the polyol when the low level of soap is used. Again, the primary advantage is the avoidance of excess material that has to be removed from the reaction mixture. The combination of the low level of soap emulsifier and the lower partial esters of the polyol provided by backmixing is effective in solubilizing the polyol, e.g., sucrose.

The combination of the low levels of excess materials improves the economics of the process and can reduce the formation of unwanted materials.

(III) Another useful improvement to combine with the above improvements (I) and/or (II) in a continuous process is (4) the removal of soap after the reaction has reached a later, subsequent stage where the soap is no longer needed to dissolve the polyol, is not soluble in the reaction mixture, and can interfere with the reaction rate.

(IV) The combination of (5) polyol removal with combinations of improvements (I) and/or (II) and/or (III) are also desirable to improve both the speed of esterification and the degree of esterification completeness. Polyol that has not been dissolved in the early stage(s) of the reaction can interfere with the degree of completion.

(V) The combination of (7) low temperature and (8) higher pressure, especially in the last stages of the reaction and more especially in the last stages of a continuous process is desirable since the combination makes it possible to fabricate the reaction apparatus without making provision for the maintenance of the more extreme conditions required by prior processes and allows for savings in energy usage in addition to the avoidance of the formation of undesirable and/or unneeded by-products. The savings are even greater in the preferred "plug-flow" final stages of the process where the conditions have to be maintained throughout the portion of the apparatus where the final stages of the reaction occur.

(VI) The combination of (9) backmixing in the initial stage(s) and (10) plug-flow conditions in the later stage(s) is highly preferred, especially for a continuous process, or mixed batch/continuous process, or continuous/batch process.

The combination of improvements (9) and (10) helps maintain optimum conditions for initiating the reaction between ingredients that are normally not compatible and then maximizing the final degree of esterification of the polyol.

(VII) Desirable further combinations are the above combination of (VI) with previously disclosed combinations of improvements (I), (II), (III), (IV) and/or (V).

(VIII) Other preferred combinations of improvements are the combination of (9) backmixing in the first stage(s) and (10) plug-flow conditions in the later stage(s) as set forth in combination (VI) and (3) the low level of soap emulsifier, and, desirably, (6) the low molar ratio of ester reactant to polyol.

This combination of improvements provides optimum conditions with minimum reactants and is especially important to ensuring consistent high degrees of esterification in a continuous process.

(IX) Another desirable combination of improvements is the combination of (6) low ester/polyol ratio; (7) low temperature; and (8) higher pressures and optionally, but preferably, (5) the removal of unreacted polyol at an early stage of the reaction; and (2) lower catalyst levels. This combination provides low levels of by-products such as difatty alkyl ketone. Difatty alkyl ketone is a typical by-product that is formed when fatty acid ester of volatile alcohol is a reactant. The majority of the difatty alkyl ketone is formed in the later stages.

The difatty alkyl ketone content is believed to be an indicator of the purity of the product. Obviously, the purer the product, the better it is.

The preferred products of the processes described herein have a detectable difatty alkyl ketone content, but one that is less than about 300 ppm, preferably less than about 200 ppm, more preferably less than about 100 ppm. The preferred products contain less than about 4,000 ppm, preferably less than about 3,000 ppm of materials other than the desired polyol polyester. However, in products made by commercial processes of the types disclosed herein there is usually a detectable level, typically more than about 50 ppm of such other materials. The very low levels of by-products are achieved by the improvements herein, using good quality methyl esters as described hereinbefore, and applying finished product clean-up procedures as described hereinafter.

The Reaction

In general, by way of example, an initial heterogeneous reaction mixture comprises from about 10% to about 30%, preferably from about 14% to about 18%, by weight of polyol; from about 0.3 to about 1.4, preferably from about 0.3 to about 0.7 moles of fatty acid ester per esterifiable site on the polyol; from about 0.001 to about 0.6, preferably from about 0.2 to about 0.4, moles of alkali metal fatty acid soap per mole of the polyol; the initial reaction stage contains an effective amount of lower partial polyol esters; and from about 0.01 to about 0.1, preferably from about 0.02 to about 0.05, mole per mole of the polyol of basic catalyst component. In general it is desirable, and even preferred, to effect the reaction in at least two stages and, preferably, in from about 3 to about 10 stages. In any later stage, additional fatty acid esters and, possibly, a more reactive catalyst can be added. In any second, or later step, additional fatty acid ester can be added to raise the overall ratio of fatty acyl groups to the esterifiable hydroxy sites on the polyol to from about 0.9:1 to about 1.4:1, preferably from about 1:1 to about 1.2:1. A preferred catalyst in the initial step is potassium carbonate, potassium methoxide, and/or residual base in the soap, as described hereinbefore and, in any later step, the preferred catalysts are potassium and/or sodium carbonates and/or methoxides.

The reaction mixture is heated to a temperature within the range from about 115° C. to about 150° C., preferably from about 130° C. to about 140° C., under a pressure of from about 5 mm to about 300 mm Hg, preferably from about 15 mm to about 100 mm Hg. It is highly preferred that the reaction mixture, or mixtures, be stirred as vigorously as possible. The temperature in subsequent stages is lowered to from about 175° F. to about 275° F., preferably from about 210° F. to about 250° F., as discussed hereinbefore. The mixing is increased in the subsequent stages by the preferred step of sparging with an inert gas, preferably nitrogen, carbon dioxide, low molecular weight hydrocarbons, oxides of nitrogen, etc. With sparging, the removal of volatile alcohol produced in the reaction is promoted and the reaction is speeded up so that the temperature can be kept low and/or the pressure can be kept higher. Low temperatures in the subsequent later stages are highly desirable to minimize the formation of unwanted by-products including di-fatty alkyl ketones, carbonyl compounds, ring structures, etc.

Finished Product Clean-Up

After the reaction has reached the desired state of completion, the catalyst, the excess fatty esters, and the emulsifier, e.g., soap, must be removed if they cannot be used in the eventual consumption of the polyol fatty acid polyesters. The soap and catalyst can be removed to a large extent by a water separation step. However, it is an advantage of the processes herein that the level of catalyst, soap, and/or unreacted polyol and/or ester reactant present can be reduced drastically. Water is added, preferably at a ratio of from about 0.5:1 to about 10:1 relative to the amount of soap being removed. This low water level which is much less than would normally be considered desirable, surprisingly results in a better removal of the soap and catalyst than is achieved with more water, e.g., 20-40%. Separation of the soap and catalyst is facilitated by passing the water and reaction mixture through a centrifuge.

After centrifugation, the reaction mix can still contain an undesirable level of residual soap and/or color bodies. It is useful to repeat the water washing step followed by gravity or centrifugal separation of the aqueous phase. A subsequent vacuum drying and adsorptive bleaching operation can be used in combination with, or instead of, this second washing step. Drying and/or adsorptive bleaching operations, that use adsorbents such as bleaching earth and/or silica gel, are typical operations for processing edible oils. The adsorbents are added, preferably at a level of from about 0.1% to about 10% by weight of the dry reaction mix. After the bleaching operation is completed, the adsorbents are removed from the reaction mixture by filtration. The second stage water washing, and/or drying, and/or adsorptive bleaching completes the removal of soap and color bodies and prepares the reaction mixture for removal of any unreacted fatty acid ester.

A useful known process that can be used, in addition to the improvements described hereinafter, for removing unreacted materials, e.g., fatty acid ester reactant, and any other undesirable materials comprises a high temperature vacuum steam distillation process, and involves deaerating the polyol polyester to a level of less than about 0.10% by volume of dissolved oxygen and heating the deaerated oil to a temperature between about 390° F. (200° C.) and about 480° F. (250° C.) and then stripping with a stripping medium in the amount of about 0.2% to about 20% by weight of the oil at an absolute pressure of less than about 15 mm Hg for a time of between about 5 seconds and about 15 minutes. This vacuum stripping at very high temperatures for short residence times minimizes the content of undesirable materials. It is desirable to either maintain the temperature below about 450° F. (230° C.), preferably less than about 350° F. (about 180° C.), in a batch deodorizer, or admix the polyol polyester with a fatty acid triglyceride to protect the polyol polyester from excessive thermal degradation. Removal of such unreacted materials and other undesirable materials can also be desirably effected in a wiped film heat exchanger or other film evaporator.

Another useful improvement in finished product clean-up, known to the inventive entity of this application, but not part of its invention, involves adding a small amount of solubilized base (e.g., potassium hydroxide or potassium methoxide, solubilized in methanol) before distillation of any excess fatty acid ester reactant. The solubilized base improves the oxidative stability of the polyol fatty acid polyesters. The solvent for the base is preferably non-aqueous and the pH, measured at 120° F. on a 10% polyol fatty acid polyester solution in water/isopropanol, is from about 6.5 to about 9.

After the initial treatments, as described hereinbefore, the undesirable materials can reform due to degradation of the oil/fatty acid ester. In addition, some undesirable color materials remain after the high temperature vacuum steam distillation process. The very low levels of color/odor/flavor materials, precursors, and/or oxidation products most preferred for use herein can be achieved by a clean-up procedure comprising one or more steps including, but not limited to:

(1) a step involving treatment with silica gel having the following properties: (a) a particle size of ranging from about 10 to about 30, preferably from about 20 to about 25 microns; (b) average pore diameter of from about 50 to about 70 microns; (c) surface area of from about 720 to about 800, preferably from about 770 to about 800 m$^2$/gm; (d) pore volume of from about 0.9 to about 1.9, preferably from about 1.2 to about 1.4 cm$^3$/gm; (e) a pH of from about 5 to about 8, preferably from about 5 to about 7.3 measured at a level of about 5% in water; and (f) total volatiles of less than about 20%, preferably from about 6.5% to about 10.5%, and more preferably from about 8% to about 10.5%. Such silica gels are extremely effective as compared to other known materials. Said silica gel is added to the product at levels of from about 0.25% to about 5%, preferably from about 1% to about 2%.

The use of the silica gel inevitably introduces oxygen, from entrapped air, into the polyester. It has been discovered, surprisingly, that oxygen can provide a benefit. Therefore, another process step involves introducing oxygen up to about saturation level, as a separate step and/or by the silica gel, and then raising the temperature to at least about 200° F. (about 90° C.), preferably at least about 380° F. (about 190° C.), but less than about 425° F. (about 220° C.), preferably less than about 400° F. (about 205° C.), to produce peroxygen groups and hold the product at the elevated temperature for a period of time sufficient to reduce the peroxygen content and/or reduce the content of colored materials present, e.g., from about 1 to about 150 minutes, preferably from about 1 to about 20 minutes, and most preferably from about 5 to about 10 minutes. (The level of oxygen in the polyol polyester is believed to be from about 0.001 to about 0.16 volumes of oxygen per volume of polyol polyester assuming similar values to those reported for triglycerides.) This can be accomplished separately, or in combination with a steam deodorization step, as described hereinbefore. The time should not be so long as to start again increasing the color. When this oxygen/heat treatment step is used, it is possible to use a wider range of silica gels in place of the preferred silica gel of step (1) and achieve acceptable results. The best results, however, are achieved with the preferred silica gel.

Any steam deodorization steps prior to the silica gel bleaching step and/or after the heat treatment step can be accomplished in the presence of a conventional triglyceride in ratios of higher polyol polyester to triglyceride of from about 1:10 to about 10:1, preferably from about 1:5 to about 5:1, more preferably from about 1:3 to about 3:1. This "codeodorization" minimizes thermal degradation of said polyester. The operating conditions for codeodorization are from about 300° F. (about 150° C.) to about 600° F. (about 315° C.), preferably from about 350-525° F. (about 175-275° C.); about 0.1-20 mm Hg (preferably about 1-10 mm Hg) vacuum; and steam to product ratio of about 0.001-0.30 (preferably 0.005-0.10). As compared to deodorization of the polyol polyester by itself, codeodorization permits the use of higher temperatures, e.g., from about 300° F. (150° C.) to about 600° F. (315° C.), preferably from about 350° F. (175° C.) to about 525° F. (275° C.), and/or longer times without excessive degradation and can be desirable if equipment limitations are present. The triglyceride is usefully any common triglyceride, e.g., those derived from cottonseed, peanut, safflower, sunflower, coconut, rapeseed, canola, palm, palm kernel, and/or soybean oils.

When the initial reactants have been properly cleaned up and the preceding clean-up steps have been applied properly, the color of the polyol polyester is less than about 3.0, preferably less than about 1.2, more preferably less than about 0.8 Lovibond Red, and the flavor grade of the polyol polyester is at least 7, preferably at least 8 panel score units (psu) as measured by a panel of experts using a grade system in which 10 is bland and 1 is severely oxidized. Such a finished polyol polyester has improved oxidative, flavor, and thermal stability during its subsequent uses. When combined with a typical triglyceride, containing natural antioxidants, in ratios of polyol polyester to triglyceride of from about 1:10 to about 10:1, preferably at ratios of from about 1:3 to about 3:1, more preferably at ratios of from about 1:3 to about 1:1, the stability is further surprisingly enhanced. Apparently, the reactive materials are reduced to a level where the natural antioxidants can provide improved long term stability.

Combinations of one or more of these cleanup steps reduce the quantity of undesired materials to a very low level, typically from about 50 ppm to about 4,000 ppm, most preferably less than about 3,000 ppm. For example, the products of the processes described herein can contain less than about 300 ppm, preferably less than about 200 ppm, more preferably less than about 100 ppm of di-fattyalkylketone which is typically present in products prepared by (fatty acid ester)/polyol interesterification reactions. This is especially true when the methyl ester excess is low and/or lower temperatures are used.

Especially preferred polyol polyesters are those which have been esterified to a level of more than about 50%, preferably more than about 70%, and more preferably more than about 80% octaester for use in preparing liquid shortenings and from about 80% to about 90% octaester for "solid" shortenings. Such sucrose polyesters have superior thermal stability, especially when they contain only low levels of color/odor materials and/or other oxidation products.

All percentages, parts and ratios herein are by weight unless otherwise specified.

EXAMPLE 1

This Example compares large particle and small particle sucrose and potassium carbonate in a batch reaction that is also representative of a continuous reaction with two stages. The reactions use a 1-liter glass reactor fitted with a thermometer, heating mantle, mechanical agitator, McLeod gauge, condenser, and temperature regulating device. Vacuum is drawn on the reactor with a mechanical vacuum pump.

To perform the first stage of the reaction, about 148 grams of partially hardened soybean methyl esters (0.5 mole) are added to the reactor along with about 25 grams of potassium stearate soap (0.08 mole), and about 1.4 grams of potassium carbonate catalyst (0.01 mole). To this mixture is added about 34.2 grams of crystalline sucrose (0.1 mole) with an average particle size of about 500 microns. This mixture is reacted at about 135° C. and about 15 mm Hg for about 1.5 hours.

To perform the second stage of the reaction, about 207 grams of partially hardened soybean methyl esters (0.7 mole) and about 1.4 grams of potassium carbonate catalyst (0.01 mole) are added to the reactor. This mixture is reacted at about 135° C. and about 2 mm Hg for an additional four hours. The reaction is sampled at approximately the 1.5 hour point, and every hour thereafter, and the samples are analyzed by supercritical fluid chromatography using an internal standard to calibrate the results. The approximate results are shown in Table 1 below.

TABLE 1A

| Time (Hours) | % Octaester | % Unreacted Sucrose |
|---|---|---|
| 1.5 | 0 | 8.00 |
| 2.5 | 0 | 3.30 |
| 3.5 | 16.5 | 0.74 |
| 4.5 | 20.5 | 0.13 |
| 5.5 | 70.2 | 0 |

The second part of this Example is run in the same apparatus, using the same method as above. The types and amounts of the reactants are the same with the exception of the sucrose and potassium carbonate. In this part, crystalline sucrose with an average particle size of about 500 microns is first ground and sieved through a 400 mesh screen so that the majority of the particles are less than about 38 microns. The potassium carbonate is also ground and sieved so that the majority of the particles are less than about 38 microns. The approximate results of the reaction with this type of sucrose and potassium carbonate is shown in Table 2 below.

TABLE 1B

| Time (Hours) | % Octaester | % Unreacted Sucrose |
|---|---|---|
| 1.5 | 0 | 1.64 |
| 2.5 | 54.0 | 0 |
| 3.5 | 77.7 | 0 |
| 4.5 | 85.9 | 0 |
| 5.5 | 89.2 | 0 |

The reduction in size of the polyol (sucrose) and/or catalyst (potassium carbonate) provides both improved reaction kinetics and improved completion.

EXAMPLE 2

This Example shows the ability to achieve good conversion to octaester using low ester/sucrose molar ratios. This Example is run the same as Example 1B except that an ester/sucrose molar ratio of 9/1 instead of 12/1 is used and the second stage is sparged with about 100 scc/min. of $N_2$. About 0.5 mole of fatty acid ester is added in the first stage of the reaction and about 0.4 mole is added in the second stage of the reaction. The approximate results of this reaction are shown in Table 3 below.

TABLE 2

| Time (Hours) | % Octaester | % Unreacted Sucrose |
|---|---|---|
| 1.5 | 0 | 1.38 |
| 2.5 | 46.5 | 0 |
| 3.5 | 76.0 | 0 |
| 4.5 | 85.9 | 0 |
| 5.5 | 87.8 | 0 |

This result compares favorably with the results of Example 1B despite using only about a 12½% excess of methylester as opposed to a 50% excess in Example 1B.

EXAMPLE 3

This Example demonstrates the ability to operate at higher pressure in the second stage of the reaction.

This reaction is run the same as Example 1B except that the second stage of the reaction is run at about 45 mm Hg, and approximately 100 scc/min. of nitrogen is sparged through the reaction mixture. The second stage of the reaction is run for about 6 hours.

TABLE 3

| Time (Hours) | % Octaester | % Unreacted Sucrose |
|---|---|---|
| 1.5 | 0 | 1.80 |
| 2.5 | 11.0 | 0 |
| 3.5 | 25.0 | 0 |
| 4.5 | 41.0 | 0 |
| 5.5 | 58.5 | 0 |
| 6.5 | 68.8 | 0 |
| 7.5 | 71.3 | 0 |

Improved results are obtained with improved mixing and more sparging.

EXAMPLE 4

This Example demonstrates the ability to operate at higher pressures and lower temperatures in the second stage of the reaction. This reaction is run the same as Example 1B, except that the second stage of the reaction is run at about 110° C., about 30 mm Hg, and with approximately 100 scc/min. of nitrogen sparged through the reaction mixture.

TABLE 4

| Time (Hours) | % Octaester | % Unreacted Sucrose |
|---|---|---|
| 1.5 | 0 | 0.82 |
| 2.5 | 0 | 0.21 |
| 3.5 | 13.9 | 0 |
| 4.5 | 52.4 | 0 |
| 5.5 | 74.9 | 0 |

The lower temperatures also give fewer reaction by-products.

EXAMPLE 5

This Example demonstrates the ability to use other types of fatty acid methyl ester. This Example uses the same apparatus as Example 1. The same type of ground sucrose and potassium carbonate catalyst as in the second part of Example 1 are also used. To perform the first stage of the reaction, about 322 grams of hardened high erucic rapeseed methyl esters are added to the reactor along with about 31 grams of ground sucrose, about 11.3 grams of potassium stearate soap and about 1.3 grams of potassium carbonate catalyst. This mixture is reacted at about 135° C. and about 2 mm Hg for about 1.5 hours.

To perform the second stage of the reaction, about 1.3 grams of potassium carbonate catalyst are added to the mixture from the first stage and this mixture is reacted at about 135° C. and about 2 mm Hg for an additional approximately six hours. The approximate results of this reaction are shown in Table 6 below.

TABLE 5

| Time (Hours) | % Octaester |
| --- | --- |
| 1.5 | 0 |
| 2.5 | 0 |
| 3.5 | 20.3 |
| 4.5 | 51.5 |
| 5.5 | 66.9 |
| 6.5 | 79.0 |
| 7.5 | 82.0 |

EXAMPLE 6

This Example demonstrates the ability to use other catalysts and to use reduced levels of catalyst. This reaction is run the same as Example 1, part 2, except that the second stage of the reaction is run with $KOCH_3$ solution (25% $KOCH_3$ in methanol by weight) instead of potassium carbonate. 0.7 grams of $KOCH_3$ solution (0.0025 mole) are used in the first stage of the reaction, and 0.7 grams in the second stage of the reaction.

TABLE 6

| Time (Hours) | % Octaester | % Unreacted Sucrose |
| --- | --- | --- |
| 1.5 | 0 | 1.57 |
| 2.5 | 0 | 0.22 |
| 3.5 | 45.8 | 0 |
| 4.5 | 77.2 | 0 |
| 5.5 | 81.4 | 0 |

EXAMPLE 7

This Example shows the ability to use lower levels of catalyst. This Example uses the same apparatus as Example 1, part 2. In this reaction, all of the ingredients are added in a single stage. The catalyst in this reaction is the residual KOH in the soap. The soap contains about 0.23% (by weight) KOH.

About 25 grams of water, about 25 grams of sucrose (0.073 moles), about 25 grams of potassium stearate soap (0.079 moles), and about 320 grams of partially hardened soybean methyl esters (1.094 moles) are added to the reactor and mixed thoroughly. The soap contains about 0.001 moles of KOH, resulting in about 0.014 mole of KOH per mole of sucrose added to the reaction mixture. The mixture is heated at about 60° C. and about 2 mm Hg until all of the water is removed. The vacuum is controlled manually in order to limit the foaming during the evaporation of the water. The mixture is then reacted at about 135° C. and about 2 mm Hg for about 5.5 hours. The results are shown in the table below.

TABLE 7

| Time (Hours) | % Octaester |
| --- | --- |
| 1.5 | 0 |
| 2.5 | 0 |
| 3.5 | 18.8 |
| 4.5 | 89.3 |
| 5.5 | 94.6 |

EXAMPLE 8

This Example 8 shows the ability to use lower levels of soap. This Example uses the same apparatus, procedure and materials that are used in Example 7, except that only about 8 grams of potassium stearate soap are used, and about 0.25 grams of potassium carbonate catalyst (0.0018 moles) are added to the initial mixture. This amount of soap amounts to about 0.344 moles of soap per mole of sucrose. The results of this reaction are shown in the table below.

TABLE 8

| Time (Hours) | % Octaester |
| --- | --- |
| 1.5 | 0 |
| 2.5 | 25.1 |
| 3.5 | 98.1 |

Examples 9 and 10 make use of a 3-liter continuous stirred tank reactor (CSTR) to perform the first stage of the reaction. The residence time of this reactor is about 1.5 hours, and the liquid volume is maintained at about 1 liter.

EXAMPLE 9

A feed mixture for the continuous reactor is prepared in a 22-liter feed tank. This feed mixture is composed of about 10686 grams of partially hardened soybean methyl esters, about 850 grams of potassium stearate soap, about 50 grams of potassium carbonate, and about 2272 grams of sucrose. The sucrose is ground and sieved so that a majority of the particles are less than about 106 microns.

The continuous reactor is started up and allowed to reach steady state. The reactor conditions are about 135° C., about 15 mm Hg, about 1 liter volume, and about 1.5 hours residence time. At steady state the product exiting from the continuous reactor has an average composition of about 3.05 fatty acid chains per molecule of sucrose, and contains about 2.11% by weight of sucrose.

About 156 grams of the steady state product from the first stage of the continuous reactor, along with about 200 grams of partially hardened soybean methyl esters and about 0.75 grams of potassium carbonate catalyst are added to the batch reactor described in Example 1. The second stage of this reaction is then run as a batch reaction for about 3 hours. The results of this reaction are shown in the table below.

TABLE 9

| 2nd Stage Batch Reaction Time (Hours) | % Octaester | % Sucrose |
|---|---|---|
| 1.0 | 46.1 | 0 |
| 2.0 | 81.3 | 0 |
| 3.0 | 97.8 | 0 |

This Example shows the effect of reduced sucrose particle size (compared to Example 9) on the level of residual sucrose in the product from a first stage continuous reaction.

EXAMPLE 10

Variation (a). A feed mixture for the continuous first stage reactor (described in Example 9) is prepared in a 22 liter feed tank. The feed mixture consists of about 10686 grams of partially hardened soybean methyl esters, about 850 grams of potassium stearate soap, about 50 grams of potassium carbonate, and about 2,272 grams of sucrose. The sucrose is ground so that a majority of the particles are less than about 200 microns.

The continuous reactor is started up and allowed to reach steady state. The reactor conditions are about 135° C. about 15 mm Hg, about 1 liter volume, and about 1.5 hours residence time.

Variation (b). A feed mixture for the continuous first stage reactor is prepared in a 22 liter feed tank. The feed mixture consists of about 10686 grams of partially hardened soybean methyl esters, about 850 grams of potassium stearate soap, about 50 grams of potassium carbonate, and about 2272 grams of sucrose. The sucrose is ground so that a majority of the particles are less than about 20 microns.

Variation (c). A feed mixture for the continuous first stage reactor (described in Example 9) is prepared in a 22 liter feed tank. The feed mixture consists of about 5,350 grams of partially hardened soybean methyl esters, about 425 grams of potassium stearate soap, about 50 grams of potassium carbonate, and about 2,272 grams of sucrose. The sucrose is ground so that a majority of the particles are less than about 10 microns.

The continuous reactor is started up and allowed to reach approximately steady state. The reactor conditions are about 135° C., about 15 mm Hg, about 1 liter volume, and about 1.5 hours residence time. The results of the first stage reactions described in variations (a), (b), and (c) are shown in the Table below.

TABLE 10

| Time (Hours) | (a) % Sucrose | (b) % Sucrose | (c) % Sucrose |
|---|---|---|---|
| 1.5 | 10.90 | 5.93 | 6.07 |
| 2.5 | 8.60 | 3.42 | 1.56 |
| 3.5 | 6.34 | 2.10 | 0.81 |
| 4.5 | 5.16 | 1.43 | 0.63 |
| 5.5 | 4.44 | 1.55 | 0.64 |
| 6.5 | 4.16 | 1.51 | 0.42 |
| 7.5 | 2.88 | 1.71 | |
| 8.5 | 3.14 | end of reaction | |
| 9.5 | 3.70 | | |
| 10.5 | 3.37 | | |
| 11.5 | 3.48 | | |
| 12.5 | 3.40 | | |
| | end of reaction | | |

As can be seen from the above results, reduction in particle size of the solid polyol (sucrose) increases the speed with which the sucrose becomes at least partially esterified. This, in turn, increases the rate of reaction for the remainder of the reaction.

EXAMPLE 11

This example demonstrates the operation of a batch process to make sucrose polyesters in which the reaction mix is filtered after the first stage and the second stage is run at higher pressures in a packed column.

The first stage of this reaction is run the same as in Example 1 except it is run in a 2-liter ractor with double the amounts of the reactants.

The second stage of the reaction is performed in a double-walled, glass column reactor that is 47 mm in diameter and packed with 3 feet of Sulzer wire gauze packing. A 2-liter receiving flask on the bottom of the column is configured so as to be able to continuously return material to the top of the column through the use of a small pump. Vacuum is applied to the top of the column. Nitrogen is sparged into the receiving flask and the nitrogen travels upward, counter-current to the downward flow of the reaction mixture. Temperature is controlled by a heating mantle or heating tape.

The second stage reactants are added in double the amounts listed in Example 1 and the reaction mixture is continued until the average degree of esterification is about 5.5. The reaction mixture is then filtered through filter paper (Whatman 934 AH) at a temperature of approximately 250° F. (about 120° C.). Particles having a diameter larger than about one micron are separated in this filtration step. The filter cake is discarded. The filtrate is collected in the column receiver during filtration under a mild vacuum. This mixture is heated to about 135° C. and continuously recirculated through the column at a rate of about 10 sccm (standard cubic centimeters per minute). Vacuum is applied and adjusted so that the pressure at the top of the column is approximately 100 mm Hg and about 120 mm Hg at the bottom. The nitrogen flow rate is approximately 175 sccm. After only about 4.5 hours the product was about 92% octaester.

This shows that fast reactions are possible at relatively high pressures through the use of sparging and filtration in a column reactor. Additionally, no recatalysis is required following the filtration, which reduces the formation of undesirable by-products.

EXAMPLE 12

This example demonstrates the ability to run the second stage of a reaction to make sucrose polyesters in a continuous fashion through a sieve tray column at high pressures and with low excess esters.

The apparatus used in this example is similar to that described in Example 11 except that a double-walled 15 sieve tray glass column is used. Additionally, there is a separate 2-liter flask from which feed is pumped to the top of the tray column, and the receiver at the bottom of the column allows removal of up to 40 ml of reaction product from an evacuated system to atmospheric pressure. The temperature of the column is maintained by circulating hot oil through the column jacket.

This example is identical to Example 11, above, through the filtration step, except that in this case only about 236 grams of partially hardened soybean methyl esters are added (0.8 mole), and the filtrate is collected in the feed flask under modest vacuum. Feed flow is then started to the top tray in the column at a rate of approximately 1.7 sccm, the temperature is adjusted to about 135° C., and the average pressure in the column is approximately 50 mm Hg. The nitrogen sparge rate is about 175 sccm. The residence time in the column is approximately 40 min. After about 0.7 hour the product is about 84% octaester.

Analysis of the product from the effluent of the column shows that the excess methyl esters have simultaneously been reduced to less than 1% via stripping during the reactive distillation.

This example illustrates that very fast reactions that are possible with high degrees of esterification in continuous second stage tray columns or other plug-flow-like devices with adequate sparging even at elevated pressures; reduced soap levels; and with low amounts of excess esters. Furthermore, the cleanup of the reaction effluent is much improved since lower amounts of excess methyl esters remain due to the stripping action of the column operation.

EXAMPLE 13

This example demonstrates the ability to utilize a series of three Continuously Stirred Tank Reactors (CSTR) for the first stage of a reaction to make sucrose polyesters using reduced soap levels and then completing the second stage of the reaction in a batch reactor.

The three CSTR reactors in series are each well agitated, 15-liter glass vessels having residence times of about 1.5 hours, 1.3 hours, and 1.5 hours, respectively, from the first in the train to the last. The feed mixture is composed of partially hardened soybean methyl esters (about 73% by weight) and sucrose ground so that a majority of the particles are less than 200 microns (about 16% by weight). A 25% slurry of potassium carbonate in partially hardened methyl esters is continuously introduced into each reactor during operation to maintain the catalyst level at about 0.2%. A separate stream of partially hardened methyl esters is introduced into both the second and third reactors of the train so that the total molar ratio of methyl esters to sucrose is 14:1.

The first reactor is started up in a batch mode using approximately 8 liters of the feed slurry, about 15 ml of the catalyst slurry and about 1,000 grams of potassium stearate soap. The reactor conditions are about 135° C. and about 15 mm Hg. Once the average composition of the product reaches about two fatty acid chains per molecule of sucrose and contains about 4% sucrose the batch operation is stopped and continuous operation is started with product from the first reactor cascading to the second and product from the second reactor cascading to the third. The temperatures for all three reactors are approximately 135° C. and the pressure is about 2 mm Hg. The reactors are allowed to reach steady-state exiting from the third reactor having an average composition of about 1% potassium soap, about 5.5 fatty acid chains per molecule of sucrose and less than about 1% sucrose.

About 350 grams of the steady-state product from the continuous reactor train is collected and added to the batch reactor described in Example 1. About 0.75 grams of potassium carbonate catalyst is added and the second stage of this reaction is then run, as a batch reaction with the following results.

| 2nd Stage Batch Reaction Time (Hrs.) | % Octaester |
|---|---|
| 3.0 | 89 |
| 4.0 | 93 |

This example shows the use of backmix reactors for the first stage of the reaction which in this case eliminated the need for adding soap to the feed. This reduction in soap level enhances the reaction rate and considerably simplifies product cleanup.

EXAMPLE 14

This example demonstrates the ability to run the reaction continuously using a series of five CSTR reactors.

The five CSTR reactors in series are each well agitated, 25 gallon vessels with external recycle loops that have pump rates of about 0.3 reactor volumes/min., and have approximately the following operating conditions.

| | Reactor Number | | | | |
|---|---|---|---|---|---|
| Parameter | 1 | 2 | 3 | 4 | 5 |
| Residence Time (hr) | 1.5 | 1.0 | 1.6 | 1.6 | 1.6 |
| Temperature (° C.) | 135.0 | 135.0 | 135.0 | 135.0 | 135.0 |
| Pressure (mm Hg) | 15.0 | 15.0 | 2.0 | 2.0 | 2.0 |
| $N_2$ Sparge (lb/hr) | 0.0 | 0.0 | 0.2 | 0.2 | 0.2 |

The sparging rate in this example can vary from about 0.01 to about 1 lb. of $N_2$ per lb. of polyol. Similar sparging rates can be used for other gases and other polyols, in other continuous polyol interesterification reactions, using substantially equivalent moles of gas per esterifiable hydroxy group on the polyol.

The feed mixture is composed of partially hardened soybean methyl esters (about 73% by weight), potassium stearate soap (about 11% by weight), and sucrose with an average particle size of about 500 microns (about 16% by weight). A 25% slurry of potassium carbonate in partially hardened methyl esters is continuously introduced into each of the first four reactors during continuous operation to maintain the catalyst level at about 0.3-0.6%. A separate stream of partially hardened methyl esters is introduced into both the second and third reactors of the train such that the total molar ratio of methyl esters to sucrose is 14:1.

The first reactor is started up in a batch mode using approximately 19 liters of the feed slurry and about 250 ml of the catalyst slurry. The batch reactor conditions are about 135° C. and about 15 mm Hg. Once the average composition of the product reaches about two fatty acid chains per molecule of sucrose and contains about 6% sucrose the batch operation is stopped and continuous operation is started with the feed slurry introduced into the first reactor and the intermediate product from the first reactor cascading to the second and so on down the train. The reactors are allowed to reach steady-state with the average composition at steady-state exiting from each reactor about the following.

|                                             | Reactor Number |      |      |      |      |
| ------------------------------------------- | -------------- | ---- | ---- | ---- | ---- |
| Parameter                                   | 1              | 2    | 3    | 4    | 5    |
| Average Fatty Acid Chains per Molecule of Sucrose | 2.7      | 3.8  | 6.3  | 7.7  | 7.9  |
| Soap (Wt. %)                                | 11.6           | 7.2  | 5.1  | 5.1  | 5.2  |
| Catalyst (Wt. %)                            | 0.3            | 0.3  | 0.4  | 0.6  | 0.6  |
| Sucrose (Wt. %)                             | 4.2            | 1.4  | 0.4  | <0.4 | <0.4 |

This example shows that good utilization and high conversions of reactants can be made continuously in a reactor cascade of CSTR's with a large sucrose particle size.

EXAMPLE 15

This example demonstrates the beneficial effects of filtering the reaction mixture after the first stage of the reaction. The reaction apparatus used in this example is similar to that used in Example 1.

To perform the first stage of the reaction, 148 grams of partially hardened soybean methyl esters (0.5 mole) are added to the reactor along with 25 grams of potassium stearate soap (0.08 mole) and 1.4 grams of potassium carbonate catalyst (0.01 mole). To this mixture is added about 34.2 grams (0.1 mole) of crystalline sucrose that is dry milled twice through a pulverizing mill. The mean particle size of this sucrose is about 23 microns. This mixture is reacted at about 135° C. and about 15 mm Hg for about 2 hours. The average degree of esterification at this point is about 2.45, and the mixture has about 2.1% unreacted sucrose.

This mixture is next filtered through filter paper that will remove all particles greater than about 1 micron (Whatman 934 AH) at about 120° C. The mixture is then returned to the reactor.

To perform the second stage of the reaction, 207 grams of partially hardened soybean methyl esters (0.7 mole) are added to the reactor. No additional catalyst is added at this point. This mixture is reacted at about 110° C. and about 2 mm Hg for an additional about 2 hours. The reaction mixture is sampled at the end of the reaction, and the sample is analyzed by supercritical fluid chromatography using an internal standard to calibrate the results. At the end of the reaction, the reaction mixture is analyzed to be about 99% octaester, and has no unreacted sucrose.

EXAMPLE 16

This example demonstrates the advantages of some preferred combinations of these improvements.

A reactor train comprising the five CSTR reactors of Example 14 are operated with the following approximate conditions:

|                       | Reactor Number |       |       |       |       |
| --------------------- | -------------- | ----- | ----- | ----- | ----- |
| Parameter             | 1              | 2     | 3     | 4     | 5     |
| Residence Time (hr)   | 1.5            | 1.5   | 2.0   | 2.0   | 2.0   |
| Temperature (° C.)    | 135.0          | 135.0 | 120.0 | 120.0 | 120.0 |
| Pressure (mm Hg)      | 15.0           | 15.0  | 40.0  | 40.0  | 40.0  |
| $N_2$ Sparge (lb/hr)  | 0.0            | 0.0   | 2.4   | 2.4   | 2.4   |

The feed mixture is composed of partially hardened soybean methyl esters (about 79% by wt.), a reduced level of potassium stearate soap (about 3% by wt.), and sucrose whose average particle size has been reduced to an average that is less than about 100 microns (about 17% by wt.). An approximately 25% slurry of potassium carbonate in partially hardened methyl esters is continuously introduced into the first two reactors during continuous operation to maintain the catalyst level at about 0.3-0.6%. Startup is similar to the process of Example 14.

Filtration of the residual, unreacted sucrose is employed between the second and third reactors (similar to Example 15). Since the reduced amount of soap is still in solution at this point, the filtration increases the soap:sucrose ratio slightly. Following filtration, there is no recatalysis (as in Example 11). If faster reactions are desired, additional catalyst ($K_2CO_3$ slurry, or reduced amounts of $KOCH_3$, as in Example 6) can be added. A separate stream of partially hardened methyl esters is introduced into both the second and third reactors of the reactor train such that, after addition, the total molar ratio of methyl esters to sucrose is about 10:1 (similar to Example 2). Following the learnings of Examples 2, 3, and 4, higher pressures, lower temperatures and larger $N_2$ sparging flows are employed in reactors three through five (versus the conditions used in Example 14).

The reactors are allowed to reach steady-state with the average composition at steady-state exiting from each reactor being about the following:

|                                             | Reactor Number |      |      |      |      |
| ------------------------------------------- | -------------- | ---- | ---- | ---- | ---- |
| Parameter                                   | 1              | 2    | 3    | 4    | 5    |
| Average Fatty Acid Chains per Molecule of Sucrose | 2.7      | 3.8  | 6.3  | 7.7  | 7.9  |
| Soap (Wt. %)                                | 3.0            | 2.2  | 1.8  | 1.8  | 1.8  |
| Catalyst (Wt. %)                            | 0.3            | 0.3  | 0.3  | 0.3  | 0.3  |
| Sucrose (Wt. %)                             | 4.2            | 1.4  | <0.1 | <0.1 | <0.1 |

The combination of reduced sucrose particle size (Example 1) and the CSTR orientation for the first stage of the reaction (Examples 9, 10 and 13) achieves excellent sucrose utilization at reduced soap levels.

The combination of sucrose filtration, lower soap levels, and high $N_2$ sparging rates achieves fast and robust reactions that reliably reach high levels of reaction completion. These combined improvements also allow the use of higher pressures, lower temperatures and reduced ester:sucrose ratios, thus improving process economics and product quality.

Similar results are achieved when a trayed column reactor, or other plug flow reactor, is substituted for the last three reactors (as described in Example 12).

What is claimed is:

1. A continuous process for preparing highly esterified polyol fatty-acid polyester by interesterifying polyol containing more than about four esterifiable hydroxy groups and fatty-acid ester of easily removable alcohol in a heterogeneous reaction mixture wherein
   a) a catalyst is used in the reaction mixture at an initial level of from about 0.01 to about 0.5 mole of catalyst per mole of polyol;
   b) a soap emulsifier is used in the initial stage of the process at a level of from about 0.001 to about 0.6 mole of soap per mole of polyol;

c) the molar ratio of total ester reactant to each esterifiable hydroxy group of the polyol in the reaction mixture ranges from about 0.9:1 to about 1.2:1;

d) the temperature in the initial stage of the process ranges from about 130° C. to about 140° C., and in the final stages of the process ranges from about 80° C. to about 120° C.; and e) easily removable alcohol is removed from the reaction mixture as the interesterifying reaction proceeds; and wherein the initial stage of the interesterifying reaction is carried out in a continuous manner under conditions of backmixing suitable for maintaining within said reaction mixture a level of lower partial fatty acid esters of said polyol that is sufficient to emulsify said reaction mixture.

2. The process of claim 1 in which the initial catalyst level is from about 0.01 to about 0.1 mole of catalyst per mole of polyol.

3. The process of claim 2 in which the catalyst level is from about 0.02 to about 0.05 mole of catalyst per mole of polyol.

4. The process of claim 1 wherein said initial level of soap emulsifier is from about 0.2 to about 0.4 mole per mole of polyol.

5. The process of claim 4 wherein said soap emulsifier is a potassium soap of hydrogenated fatty acid containing from about 10 to about 22 carbon atoms.

6. The process of claim 1 wherein said molar ratio of said total ester reactant to said esterifiable hydroxy group is from about 1:1 to about 1.2:1.

7. The process of claim 1, wherein the temperature in said initial stage is between about 132° C. and about 135° C.

8. In a continuous process for preparing highly esterified polyol fatty acid polyester by interesterifying polyol containing more than four esterifiable hydroxy groups and fatty acid ester of an easily removable alcohol in a heterogeneous reaction mixture wherein said easily removable alcohol is removed from said reaction mixture as the reaction proceeds, the improvement which comprises:

(A) carrying out an initial stage of the interesterifying reaction in a continuous manner under conditions of backmixing suitable for maintaining within said reaction mixture a level of lower partial fatty acid esters of said polyol that is sufficient to emulsify said reaction mixture; and (B) carrying out at least a final stage of the interesterifying reaction in a continuous manner under conditions approaching plug-flow conditions after the degree of esterification of said polyol has reached at least about 50%.

9. The process of claim 8 wherein the initial stage of said interesterifying reaction is carried out under conditions of backmixing until the average degree of esterification of the polyol is from about 20% to about 70%, to thereby provide sufficient lower partial polyol polyester to aid in solubilization of the polyol.

10. The process of claim 9 wherein the initial stage of said interesterifying reaction is carried out under conditions of backmixing until the average degree of esterification of the polyol is from about 35% to about 60%.

11. The process of claim 9 which is carried out in a series of at least two reaction vessels.

12. The process of claim 11 wherein there are from three to about eight of said reaction vessels.

13. The process of claim 8 wherein, in the initial stage of the interesterifying reaction, the reaction mixture contains soap emulsifier at a level of from about 0.001 to about 0.6 mole per mole of polyol.

14. The process of claim 13 wherein said soap emulsifier is at a level of from about 0.2 to about 0.4 mole per mole of polyol and said conditions of backmixing are continued until the degree of esterification of said polyol is from about 30% to about 60%.

15. The process of claim 13 wherein the final stages of the reaction are carried out under plug-flow conditions, after the degree of esterification of said polyol has reached at least about 50%.

16. The process of claim 15 wherein the molar ratio of said total ester reactant to each said esterifiable hydroxy group of said polyol is from about 1:1 to about 1.2:1.

17. The process of claim 8 wherein the temperature in the initial stage is from about 132° C. to about 135° C. and the temperature in the subsequent stages is from about 100° C. to about 120° C.

18. The process of claim 8 wherein said molar ratio of said total ester reactant to each said esterifiable hydroxy group is from about 1:1 to about 1.2:1.

19. The process of claim 8 wherein the final degree of esterification of said polyol reaches at least about 70%.

20. The process of claim 19 wherein the final average degree of esterification of the polyol is at least about 95%.

21. A process for the synthesis of polyol fatty-acid polyesters by reacting a polyol and a fatty-acid lower-alkyl ester under substantially solvent free conditions in the presence of a catalyst and an emulsifier, the process comprising an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters.

22. The process according to claim 21 wherein the reaction mixture from the initial stage is further reacted to said polyol fatty acid polyesters after combining with any remaining part of the fatty-acid lower-alkyl ester reactant.

23. A process according to claim 21 wherein the emulsifier is an alkali metal soap.

24. A process according to claim 21 wherein the alkali metal soap is selected from the group of soaps having a chain length within the range of from 8 to 22 carbon atoms.

25. A process according to claim 21 wherein the fatty-acid lower-alkyl ester is a fatty-acid methyl ester.

26. A process according to claim 21 wherein the catalyst is selected from the group consisting of potassium hydroxide and carbonates of potassium and sodium.

27. A process according to claim 21 wherein the reaction mixture in said initial reaction stage has a degree of esterification of within the range of from 10 to 60%.

28. A process according to claim 21 wherein the reaction mixture in said initial stage does not contain any substantial amount of solvent.

29. A process according to claim 21 wherein the reaction temperature in said initial stage is maintained at a level of within the range of from 130° to 140° C.

30. A process according to claim 21 wherein the average residence time of the reaction mixture in said initial stage is caused to be about 1.5 hours.

31. A process according to claim 21 wherein the molar ratio of catalyst to polyol in said initial reaction stage is within the range of from about 0.01:1 to about 0.5:1.

32. A process according to claim 21 wherein the molar ratio of emulsifier to polyol in said initial reaction stage is within the range of from 0.2:1 to 0.6:1.

33. A process according to claim 21 for the synthesis of polyol fatty-acid polyesters having a degree of esterification of at least about 70%.

34. A process according to claim 21 wherein the polyol is sucrose.

35. A process according to claim 34 wherein the molar ratio of fatty-acid lower-alkyl ester to sucrose is within the range of from 7.2:1 to 15:1.

36. A process according to claim 21 wherein said initial reaction stage is fully separate from said one or more subsequent reaction stages.

37. A process according to claim 21, wherein the partial vapor pressure of the volatile alcohol in the initial reaction stage is less than 100 mm Hg.

38. A process according to claim 37, wherein the partial vapor pressure of the volatile alcohol is maintained by sparging with an inert gas.

39. A process according to claim 21, wherein the one or more subsequent reaction zones are provided in a tray reactor.

40. A process according to claim 21, wherein the emulsifier is used in the initial reaction stage in an amount of from about 3% to about 11% by weight of the reactants.

41. A process according to claim 21, wherein the initial reaction stage is carried out in a continuous reaction vessel having stirring means.

42. A process according to claim 41, wherein in the initial reaction stage the stirring means applies agitation to ensure thorough mixing of the reaction components.

43. A process according to claim 21, wherein the initial reaction stage is carried out in a continuous stirred tank reactor.

44. A process according to claim 43, wherein the fatty-acid lower-alkyl ester is an ester of volatile $C_1$-$C_4$ alcohol.

45. A process according to claim 44, wherein the catalyst is selected from the group consisting of alkali metals, alloys of two or more alkali metals, alkali metal hydrides, alkali metal alkoxides, potassium carbonate, sodium carbonate, barium carbonate, potassium hydroxide and mixtures thereof.

46. A process according to claim 45, wherein the initial reaction stage temperature is in the range of from about 130° C. to about 140° C.

47. A process according to claim 46, wherein the emulsifier is soap.

48. A process according to claim 21, wherein the steady-state reaction mixture in the first zone is capable of solubilizing the polyol.

49. A process according to claim 21, wherein the final degree of esterification is 95% or more.

50. A process according to claim 21, wherein the final degree of esterification is 98% or more.

51. A process according to claim 21, wherein the fatty-acid lower-alkyl ester is an ester of a volatile $C_1$-$C_4$ alcohol.

52. A process according to claim 51, wherein the catalyst is selected from the group consisting of alkali metals, alloys of two or more alkali metals, alkali metal hydrides, alkali metal alkoxides, potassium carbonate, sodium carbonate, barium carbonate, potassium hydroxide and mixtures thereof.

53. A process according to claim 52, wherein the molar ratio of fatty-acid lower-alkyl ester to esterifiable sites on the polyol is from about 0.9:1 to about 1.4:1.

54. A process according to claim 52, wherein soap is used in the initial reaction stage in an amount of from about 3% to about 11% by weight of the reactants.

55. A process according to claim 52, wherein the emulsifier introduced into the initial reaction stage is soap.

56. A process according to claim 55, wherein the polyol is sucrose and reaction mixture product from the initial stage comprises not more than 4.2% unreacted sucrose.

57. A process according to claim 56, wherein the initial reaction stage temperature is in the range of from about 130° C. to about 140° C.

58. A process according to claim 57, wherein the initial reaction stage is carried out in a continuous stirred tank reactor.

59. A process according to claim 57, wherein the initial reaction stage is carried out in a continuous reaction vessel having stirring means.

60. A process according to claim 51, wherein the catalyst is selected from the group consisting of sodium carbonate, potassium carbonate, potassium hydroxide and mixtures thereof.

61. A process according to claim 51, wherein in the initial reaction stage the degree of esterification is between about 10% and about 70%.

62. A process according to claim 21, wherein the initial reaction stage is carried out in a continuous stirred reaction vessel having stirring means, wherein in the initial reaction stage the degree of esterification is between about 10% and about 70%, and wherein the fatty-acid lower-alkyl ester is an ester of a volatile $C_1$-$C_4$ alcohol.

63. A process according to claim 62, wherein in the initial reaction stage the stirring means applies agitation to ensure thorough mixing of the reaction components.

64. A process according to claim 63, wherein the initial reaction stage temperature is in the range of from about 130° C. to about 140° C.

65. A process for the synthesis of polyol fatty-acid polyesters by reacting a polyol and a fatty-acid lower-alkyl ester of a volatile $C_1$-$C_4$ alcohol under substantially solvent free conditions in the presence of a catalyst and an emulsifier, the process comprising:

an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters.

66. A process according to claim 65, wherein the fatty-acid lower-alkyl ester is a fatty-acid methyl ester.

67. A process according to claim 65, wherein there is one in-going reactant stream in the initial stage.

68. A process according to claim 65, wherein the emulsifier is used in the initial reaction stage in an amount of from about 3% to about 11% by weight of the reactants.

69. A process for the synthesis of polyol fatty-acid polyesters by reacting a polyol and a fatty-acid lower-alkyl ester under substantially solvent free conditions in the presence of a catalyst selected from the group consisting of alkali metals, alloys of two or more alkali metals, alkali metal hydrides, alkali metal alkoxides, potassium carbonate, sodium carbonate, barium carbonate, potassium hydroxide and mixtures thereof, and an emulsifier, the process comprising:

an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters.

70. A process according to claim 69, wherein the fatty-acid lower-alkyl ester is an ester of a volatile $C_1$-$C_4$ alcohol.

71. A process according to claim 69, wherein the catalyst is selected from the group consisting of sodium carbonate, potassium carbonate, potassium hydroxide and mixtures thereof.

72. A process for the synthesis of polyol fatty-acid polyesters by reacting a polyol and a fatty-acid lower-alkyl ester under substantially solvent free conditions in the presence of a catalyst selected from the group consisting of alkali metals, alloys of two or more alkali metals, alkali metal hydrides, alkali metal alkoxides, potassium carbonate, sodium carbonate, barium carbonate, potassium hydroxide and mixtures thereof, and an emulsifier, the process comprising:

an initial reaction stage wherein the temperature is in the range of from about 130° C. to about 140° C., which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters.

73. A process according to claim 72, wherein the emulsifier is used in the initial reaction stage in an amount of from about 3% to about 11% by weight of the reactants.

74. A process for the synthesis of polyol fatty-acid polyesters by reacting a polyol and a fatty-acid lower-alkyl ester under substantially solvent free conditions in the presence of a catalyst and an emulsifier, the process comprising:

an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters;

wherein the conditions in the initial reaction stage provide a stable heterogeneous reaction mixture.

75. A process for the synthesis of polyol fatty-acid polyesters by reacting a polyol and a fatty-acid lower-alkyl ester under substantially solvent free conditions in the presence of a catalyst and an emulsifier, the process comprising:

an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters;

wherein the conditions in the initial reaction stage aid in solubilizing the polyol.

76. A process for the synthesis of polyol fatty-acid polyesters by reacting a polyol and a fatty-acid lower-alkyl ester under substantially solvent free conditions in the presence of a catalyst and an emulsifier, the process comprising:

an initial reaction stage which is carried out under such conditions that the reaction mixture in said initial stage is in steady-state, with continuous introduction of reactants comprising polyol and fatty-acid lower-alkyl ester, and continuous removal of products comprising reaction mixture having a degree of esterification of about 10% or more and volatile alcohol formed during the initial reaction stage, and one or more subsequent reaction stages in which the reaction mixture from said initial stage is further reacted to said polyol fatty-acid polyesters;

wherein the conditions in the initial reaction stage aid in solubilizing the polyol and provide a stable heterogeneous reaction mixture.

* * * * *